US011466051B2

(12) United States Patent
Jensen

(10) Patent No.: US 11,466,051 B2
(45) Date of Patent: Oct. 11, 2022

(54) STABILISED PROTEIN SOLUTIONS

(71) Applicant: Novo Nordisk A/S, Bagsvaerd (DK)

(72) Inventor: Ole Elvang Jensen, Vanloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 259 days.

(21) Appl. No.: 14/396,389

(22) PCT Filed: Mar. 15, 2013

(86) PCT No.: PCT/EP2013/055390
§ 371 (c)(1),
(2) Date: Oct. 23, 2014

(87) PCT Pub. No.: WO2013/170977
PCT Pub. Date: Nov. 21, 2013

(65) Prior Publication Data
US 2015/0086566 A1 Mar. 26, 2015

Related U.S. Application Data

(60) Provisional application No. 61/651,598, filed on May 25, 2012.

(30) Foreign Application Priority Data

May 14, 2012 (EP) ..................... 12167958

(51) Int. Cl.
*C07K 1/34* (2006.01)
*C07K 16/24* (2006.01)
*A61K 39/395* (2006.01)

(52) U.S. Cl.
CPC .......... *C07K 1/34* (2013.01); *A61K 39/39591* (2013.01); *C07K 16/24* (2013.01); *C07K 16/244* (2013.01); *C07K 2317/94* (2013.01)

(58) Field of Classification Search
CPC ..................................................... C07K 1/34
See application file for complete search history.

(56) References Cited

U.S. PATENT DOCUMENTS

| | | | | |
|---|---|---|---|---|
| 5,248,767 | A | * 9/1993 | Muller | C07K 16/00 424/176.1 |
| 5,656,730 | A | 8/1997 | Lee | |
| 2003/0190316 | A1 | 10/2003 | Kakuta et al. | |
| 2004/0170623 | A1* | 9/2004 | Arvinte | A61K 9/0019 424/131.1 |
| 2005/0214278 | A1 | 9/2005 | Kakuta et al. | |
| 2006/0182740 | A1 | 8/2006 | Yang et al. | |
| 2008/0200656 | A1 | 8/2008 | Sek et al. | |
| 2009/0226530 | A1* | 9/2009 | Lassner | A61P 7/10 514/1.1 |
| 2010/0111853 | A1* | 5/2010 | Hickman | A61P 1/00 424/1.49 |

FOREIGN PATENT DOCUMENTS

| | | | | |
|---|---|---|---|---|
| CN | 1257874 | A | 6/2000 | |
| DK | WO 2010000721 | A1 * | 1/2010 | ........... C07K 16/244 |
| EP | 1610820 | A1 | 1/2006 | |
| JP | S62292731 | A | 12/1987 | |
| JP | 2006126202 | A | 5/2006 | |
| WO | 2002096457 | A2 | 12/2002 | |
| WO | 2010000721 | A1 | 1/2010 | |
| WO | WO-2010000721 | A1 * | 1/2010 | ........... C07K 16/244 |
| WO | 2010/014708 | A2 | 2/2010 | |
| WO | 2010056550 | A1 | 5/2010 | |
| WO | 2010141039 | A1 | 12/2010 | |
| WO | 2011088120 | A1 | 7/2011 | |
| WO | 2011/104381 | A2 | 9/2011 | |

OTHER PUBLICATIONS

Teeters (Biotech.Bioeng. 2011; 108:1338-1346.*
Teeters et al. Predicting diafiltration solution compositions for final ultrafiltration/diafiltration steps of monoclonal antibodies. Biotech. Bioeng. 2011; 108:1338-1346.*
Miao et al. Theoretical analysis of excipient concentrations during the final ultrafiltration/diafiltration step of therapeutic antibodies. Biotechnology Progress, 2009; 25(4):964-972.*
Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25.*
Tzannis et al. Activity_Stability Considerations of Trypsinogen during Spray Drying: Effects of Sucrose. Journal of Pharmaceutical Sciences, 1999; 88(3):351-359).*
Chang et al. (Chang, B.S. and Hershenson, S. 2002. Practical approaches to protein formulation development in "Rationale Design of stable protein formulations-theory and practice" (Year: 2002).*
Miao et al. (Biotechnology Progress, 2009; 25(4):964-972 (Year: 2009).*
Miao et al. Theoretical analysis of excipient concentrations during the final ultrafiltration/diafiltration step of therapeutic antibody. Biotechnology Progress, 2009; 25(4):964-972 (Year: 2009).*
Tzannis et al. Journal of Pharmaceutical Sciences, 1999; 88(3):351-359) (Year: 1999).*
Chang, B.S. and Hershenson, S. 2002. Practical approaches to protein formulation development in "Rationale Design of stable protein formulations—theory and practice" (J.F. Carpenter and M.C. Manning eds.) Kluwer Academic/Plenum publishers, New York. pp. 1-25 (Year: 2002).*
Teeters et al. Biotechnol Bioeng. Jun. 2011;108(6):1338-46. doi: 10.1002/bit.23067. Epub Feb. 19, 2011) (Year: 2011).*
Giuseppe Graziano, How does sucrose stabilize the native state of globular proteins? "International Journal of Biological Macromolecules" Year 2012, vol. 50, pp. 230-235.

(Continued)

*Primary Examiner* — Vanessa L. Ford
*Assistant Examiner* — Sandra Dillahunt
(74) *Attorney, Agent, or Firm* — Jianjie Hu

(57) ABSTRACT

The invention relates to a method of stabilizing highly concentrated protein solutions during ultrafiltration by addition of sucrose to the highly concentrated protein solution, in particular, but not exclusively to a method of stabilizing highly concentrated antibody solutions during ultrafiltration by addition of sucrose to the highly concentrated antibody solution.

14 Claims, No Drawings

(56) References Cited

OTHER PUBLICATIONS

Krishnan S et al. Aggregation of Granulocyte Colony Stimulating Factor under Physiological Conditions: Characterization and Thermodynamic Inhibition, "Biochemistry" Year 2002, vol. 41, pp. 6422-6431.

Lee J. C et al. The Stabilization of Proteins by Sucrose, "The Journal of Biological Chemistry" Year 1981, vol. 256, No. 14, pp. 7193-7201.

Fudo Miao et al., Theoretical Analysis of Excipient Concentrations During the Final Ultrafiltration/Diafiltration Step of Therapeutic Antibody, "Biotechnol. Prog." Year 2009, vol. 25, No. 4, pp. 964-972.

Steven J Shire, Formulation and manufacturability of biologies, "Current opinion in Biotechnology" Year 2009, vol. 20, No. 6, pp. 708-714.

Teeters Mark et al. Predicting Diafiltration Solution Compositions for final Ultrafilteration steps of Monoclonal Antibodies, "Biotechnology and Bioengineering" Year 2011, vol. 108, No. 6, pp. 1338-1346.

Ueda T et al. Aggregation and Chemical Reaction in Hen Lysozyme Caused by Heating at pH 6 are Depressed by Osmolytes, Sucrose and Trehalose1, "J. Biochem" Year 2001, vol. 130, pp. 491-496.

Wang B et al. Impact of Sucrose Level on Storage Stability of Proteins in Freeze-Dried Solids: II. Correlation of Aggregation Rate with Protein Structure and Molecular Mobility, "Journal of Pharmaceutical Sciences" Year 2009, vol. 98, No. 9, pp. 3145-3166.

Pete Gagnon, Purification Tools for Monoclonal Antibodies, Year 1996.

Krishnan S et al., Inhibition of Protein Aggregation by Sucrose (http://abstracts.aaps.org/SecureView/AAPSJournal/6hc4dycm61j7s0mebwuh.htm) Retrived on Sep. 30, 2014.

Tzannis et al., "Moisture Effects on Protein-Excipient Interactions in Spray-Dried Powders Nature of Destabilizing Effects of Sucrose," Journal of Pharmaceutical Sciences, 1999, vol. 88, No. 3, pp. 360-370.

Chang et al., "Practical Approaches To Protein Formulation Development," Pharmaceutical Biotechnology, 2002, vol. 13, pp. 1-25.

Hashemi et al., "Evaluation of Effective Parameters on the Concentrating of Anti-RH (D) Immunoglobulin Preparations Using Ultrafiltration System," Iranian Journal of Basic Medical Sciences, 2007, vol. 10, No. 1, Abstract.

Hashemi et al., "Evaluation of Effective Parameters on the Concentrating of Anti-RH (D) Immunoglobulin Preparations Using Ultrafiltration System," Iranian Journal of Basic Medical Sciences, 2007, vol. 10, No. 1, pp. 66-74, Iranian text.

Hashemi et al., "Evaluation of Effective Parameters on the Concentrating of Anti-RH (D) Immunoglobulin Preparations Using Ultrafiltration System," Iranian Journal of Basic Medical Sciences, 2007, vol. 10, No. 1, pp. 66-74, English translation.

Kamerzell et al., "Protein Excipient Interactions: Mechanisms and Biophysical Characterization Applied to Protein Formulation Development," Advanced Drug Delivery Reviews, 2011, vol. 63, pp. 1118-1159.

Vazquez-Rey et al., "Aggregates in Monoclonal Antibody Manufacturing Processes," Biotechnology and Bioengineering, 2011, vol. 108, No. 7, pp. 1494-1508.

Warne, "Development of High Concentration Protein Biopharmaceuticals: The Use of Platform Approaches in Formulation Development," European Journal of Pharmaceutics and Biopharmaceuticals, 2011, vol. 78, pp. 208-212.

Millipore Technical Brief: Protein Concentration and Diafiltration by Tangential Flow Filtration, 2003.

\* cited by examiner

STABILISED PROTEIN SOLUTIONS

CROSS-REFERENCE TO RELATED APPLICATIONS

This application is a 35 U.S.C. § 371 National Stage application of International Application PCT/EP2013/055390 (WO2013/170977), filed Mar. 15, 2013, which claimed priority of European Patent Application 12167958.3, filed May 14, 2012; this application claims priority under 35 U.S.C. § 119 of U.S. Provisional Application 61/651,598; filed May 25, 2012; all of which are incorporated by reference.

The current invention relates to ultrafiltration of concentrated protein containing solutions, particularly ultrafiltration of concentrated antibody containing solutions, particularly stabilisation of such solutions during ultrafiltration.

BACKGROUND

A number of injectable protein containing solutions, particular antibody containing solutions are supplied to the market. The use of those solutions for subcutaneous injection, results in demand of high concentration of solutions due to limitations on injection volume.

General methods for purification of antibodies are well-known in the art and are for instance described in Pete Gagnon: Purification Tools for monoclonal Antibodies (1996) ISBN-9653515-9-9.

After purification of the antibody in solution, the concentration of the antibody is increased by use of ultrafiltration (UF) and then, at some point (usually around a concentration of 50 g/L antibody (mAb), the formulation buffer is diafiltrated into the solution by ultrafiltration, then the formulated solution is usually further concentrated to its final concentration of between 100 g/L and 300 g/L, without sucrose, which normally will be added to the product after final ultrafiltration concentration. During concentration of protein/antibodies by ultrafiltration, the protein concentration at the membrane surface, the so called wall concentration may increase to high levels. This can prove harmful to the protein/antibody and causes it to denature and precipitate. This is often assumed to be the reason for observed differences in the calculated protein concentration and the measured protein concentration.

The problem with different concentration by calculation on basis of reduction factors against the actual measured concentration by UV280 nm absorbance in the retentate affects the yield of the ultrafiltration process. The know solution to this problem is to try to recover the protein by washing the module several times with buffers but the recovered protein will appear in greatly reduced concentrations.

It is therefore a need for a method that solves the problem of denaturation and precipitation of high concentrated protein solutions during ultrafiltration.

It has been shown that high concentration of sucrose in protein solutions can stabilize the protein in solution, especially against aggregation during prolonged storage of such solutions. However, the risk of infections may have resulted in avoiding sucrose as a component during ultrafiltration or other purification or concentration steps.

SUMMARY

The present invention provides a method of ultrafiltration of a highly concentrated protein solution. The present invention furthermore provides a method of stabilizing a highly concentrated protein solution during ultrafiltration.

The present invention provides a method of ultrafiltration of a highly concentred protein solution herein the protein solution is stabilized during the ultrafiltration by addition of sucrose to the solution. The present invention furthermore provides a method of ultrafiltration of a highly concentred protein solution, wherein the protein is an antibody.

DESCRIPTION

The present invention provides a method of ultrafiltration of a highly concentrated protein solution. The present invention furthermore provides a method of stabilizing a highly concentrated protein solution during ultrafiltration.

It has surprisingly been discovered that the addition of sucrose to a highly concentrated protein solution before further concentration by ultrafiltration seems to protect the protein from denaturating and precipitating during ultrafiltration. This results in higher yield or recovery % of the protein and less turbidity and formation of aggregates, as measured by % HMWP during the ultrafiltration.

The term "protein", "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, y-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (a-aminoisobutyric acid), Abu (α-aminobutyric acid), Tle (tert-butylglycine), β-alanine, 3-aminomethyl benzoic acid and anthranilic acid.

The term "antibody" and/or "mAb" as used herein covers monoclonal antibodies (including full length antibodies which have an immunoglobulin Fc region), antibody compositions with polyepitopic specificity, bispecific antibodies, diabodies, and single-chain molecules, as well as antibody fragments (e.g., Fab, F(ab)$_2$, and Fv).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein may extend to include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)).

Examples of suitable antibodies, which may be formulated in a stable composition of the invention include: 3F8, Abagovomab, Abciximab, ACZ885 (canakinumab), Adalimumab, Adecatumumab, Afelimomab, Afutuzumab, Alacizumabpegol, Alemtuzumab, Altumomabpentetate, Anatumomabmafenatox, Anrukinzumab (IMA-638), Apolizumab, Arcitumomab, Aselizumab, Atlizumab (tocilizumab), Atorolimumab, Bapineuzumab, Basiliximab, Bavituximab, Bectumomab, Belimumab, Bertilimumab, Besilesomab, Bevacizumab, Biciromab, Bivatuzumabmertansine, Blinatumomab, Brentuximabvedotin, Briakinumab, Canakinumab, Cantuzumabmertansine, Capromabpendetide, Catumaxomab, Cedelizumab, Certolizumabpegol, Cetuximab, Citatuzumabbogatox, Cixutumumab, Clenoliximab, Clivatuzumabtetraxetan, ONTO 148 (golimumab), ONTO 1275 (ustekinumab), Conatumumab, Dacetuzumab, Daclizumab, Denosumab, Detumomab, Dorlimomabaritox, Dorlixizumab, Ecromeximab, Eculizumab, Edobacomab, Edrecolomab, Efalizumab, Efungumab, Elsilimomab, Enlimomabpegol, Epitumomabcituxetan, Epratuzumab, Erlizumab, Ertumaxomab, Etaracizumab, Exbivirumab, Fanolesomab, Faralimomab, Felvizumab, Fezakinumab, Figitumumab, Fontolizumab, Foravirumab, Fresolimumab, Galiximab, Gantenerumab, Gavilimomab, Gemtuzumabozogamicin, Golimumab, Gomiliximab, Ibalizumab, Ibritumomabtiuxetan, Igovomab, Imciromab, Infliximab, Intetumumab, Inolimomab, Inotuzumabozogamicin, Ipilimumab, Iratumumab, Keliximab, Labetuzumab, Lebrikizumab, Lemalesomab, Lerdelimumab, Lexatumumab, Libivirumab, Lintuzumab, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, MYO-029 (stamulumab), Nacolomabtafenatox, Naptumomabestafenatox, Natalizumab, Nebacumab, Necitumumab, Nerelimomab, Nimotuzumab, Nofetumomabmerpentan, Ocrelizumab, Odulimomab, Ofatumumab, Omalizumab, Oportuzumabmonatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO 140, Rafivirumab, Ramucirumab, Ranibizumab, Raxibacumab, Regavirumab, Reslizumab, Rilotumumab, Rituximab, Robatumumab, Rontalizumab, Rovelizumab, Ruplizumab, Satumomab, Sevirumab, Sibrotuzumab, Sifalimumab, Siltuximab, Siplizumab, Solanezumab, Sonepcizumab, Sontuzumab, Stamulumab, Sulesomab, Tacatuzumabtetraxetan, Tadocizumab, Talizumab, Tanezumab, Taplitumomabpaptox, Tefibazumab, Telimomabaritox, Tenatumomab, Teneliximab, Teplizumab, TGN1412, Ticilimumab (tremelimumab), Tigatuzumab, TNX-355 (ibalizumab), TNX-650, TNX-901 (talizumab), Tocilizumab (atlizumab), Toralizumab, Tositumomab, Trastuzumab, Tremelimumab, Tucotuzumabcelmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, Zolimomabaritox and the like.

In one embodiment, the protein is an immunoglobulin. In one embodiment, the protein is an antibody. In one embodiment, the protein is a monoclonal antibody (mAb). In one embodiment, the protein is an IgG4 antibody.

In one embodiment, the antibody is amonoclonal anti-IL20 antibody. In one embodiment, the antibody is an anti-IL20 antibody as described in WO2010/000721. In one embodiment, the anti-IL20 monoclonal antibody is 15D2 or 5B7 as described in WO2010/000721.

It will be appreciated that the invention finds particular utility where the protein is present in solution to be ultrafiltrated in high concentrations. Thus, in one embodiment, the protein is present in a concentration of 40 g/L or more in the solution to be ultrafiltrated, such as 40, 45, 40, 55, 60, 65, 70, 75, 80, 85, 90, 95, 100, 110, 120, 130, 140, 150, 175, 200, 250, 300 g/L or more.

The final ultrafiltration retentate will have higher protein concentrations, such as in an amount of between 75 g/L and 400 g/L, for instance between 75 g/L and 350 g/L, such as between 75 g/L and 300 g/L, for instance between 100 g/L and 250 g/L, such as between 75 g/L and 200 g/L, for instance between 75 g/L and 150 g/L, such as between 75 g/L and 100 g/L. In one embodiment, the protein is present in the ultrafiltration retentate in a concentration of between 100 g/L and 400 g/L, for instance between 100 g/L and 350 g/L, such as between 100 g/L and 300 g/L, for instance between 100 g/L and 250 g/L, such as between 100 g/L and 200 g/L, for instance between 100 g/L and 150 g/L. In one embodiment, the protein is present in the ultrafiltration retentate a concentration of between 125 g/L and 400 g/L, for instance between 125 g/L and 350 g/L, such as between 125 g/L and 300 g/L, for instance between 125 g/L and 250 g/L, such as between 125 g/L and 200 g/L, for instance between 125 g/L and 150 g/L. In one embodiment, the protein is present in a concentration between 150 g/L and 400 g/L, such as between 150 g/L and 350 g/L, for instance between 150 g/L and 300 g/L, such as between 150 g/L and 250 g/L, for instance between 150 g/L and 200 g/L.

The term "stability" of a protein in a composition as used herein refers to the biological stability, physical stability or chemical stability of the protein in solution. Chemical covalent changes in the protein structure leading to formation of chemical degradation products with potential less biological potency and/or potential increased immunogenic properties compared to the native protein structure, during manufacturing process. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein composition is well-known by the person skilled in the art. Most proteins are prone to deamidation, a process in which the side chain amide group in glutaminyl or asparaginyl residues is hydrolysed to form a free carboxylic acid. Other degradation pathways involve formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals, Ahern. T. J. & Manning M. C., Plenum Press, New*

York 1992). Oxidation (of for instance methionine residues) can be mentioned as another variant of chemical degradation. The chemical stability of the protein composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

There are various analytical techniques for measuring protein stability available in the art (*Peptide and Protein Drug Delivery*, 247-301, Vincent Lee Ed. & Marcel Dekker, N.Y. Pubs 1991; and Jones, A. *Adv. Drug Delivery Rev.* 10: 29-90, 1993).

SEC-HPLC is in particular used for quantification of protein aggregates. The samples may for instance be analysed using a TSK G3000 SWXL column, isocratic elution and subsequent UV detection at 214 or 280 nm. This method is used to determine monomeric IgG content and % High Molecular Weight Proteins (HMWP) consisting of dimeric species or larger which are separated according to size by the gel resin. The monomeric content and % HMWP are determined relative to the total protein content detected by the method.

Physical stability of protein solution can be measured by well-known methods, including measurement of attenuation of light by measurement of absorbance or optical density. Such measurements relate to the turbidity of solution.

The term "turbidity" of a solution as used herein refer to the presence of cloudiness or haze in the protein solution. In protein solutions, turbidity is typically measured using a UV-visible spectrophotometer at wavelengths between 320-800 nm. The degree of turbidity can be calculated by reference to a standard curve generated by solutions with known turbidity. For protein containing pharmaceutical solutions, reference standards can be based on the European Pharmacopeia (Ph. Eur.) Section 2.2.1, that defines visual clarity and describes standard levels of turbidity in relation to water.

The term ultrafiltration (UF) as used herein refers to a variety of membrane filtration in which hydrostatic pressure forces a liquid or a solution against a semipermeable membrane. Solutes of high molecular weight are retained (retentate), while water and low molecular weight solutes pass through the membrane (permeate or filtrate). This separation process is used in industry and research for purifying and concentrating macromolecular ($10^3$-$10^6$ Da) solutions, especially protein solutions. Ultrafiltration is especially applied in cross-flow filtration mode. The term retentate, as used herein, refers to what is retained, that is the portion or content of the liquid or solution that does not pass through the ultrafiltration membrane. The term filtrate, as used herein, refers to the portion or part of the liquid or solution that does pass the membrane during ultrafiltration and is not retained.

Concentration factor is a number which is reciprocal to the volume reduction of the retentate during ultrafiltration concentration. When the retentate volume is reduced to ½, the concentration factor will be 2. The term "calculated concentration" as used herein refers to an estimated concentration that is calculated by multiplying the original mAb concentration by the concentration factor.

The term "yield" or "recovery %" as used herein, refers to the amount of protein recovered in during the ultrafiltration step or steps, in the retentate or retentates if multiply ultrafiltration or washing steps have been performed, compared with the total amount of protein in the starting protein solution to be ultrafiltrated.

The term cross-flow filtration as used herein refers to a protein purification method, also known as tangential flow filtration that is a type of filtration (a particular unit operation). Cross-flow filtration is different from dead-end filtration in which the feed is passed through a membrane or bed, the solids being trapped in the filter and the filtrate being released at the other end. Cross-flow filtration gets its name because the majority of the feed flow travels tangentially across the surface of the filter, rather than into the filter. The principal advantage of this is that the filter cake (which can blind the filter) is substantially washed away during the filtration process, increasing the length of time that a filter unit can be operational. It can be a continuous process, unlike batch-wise dead-end filtration.

In cross-flow filtration, the feed is passed across the filter membrane (tangentially) at positive pressure relative to the permeate side. A proportion of the material which is smaller than the membrane pore size passes through the membrane as permeate or filtrate; everything else is retained on the feed side of the membrane as retentate.

The volume of the fluid is reduced by allowing permeate flow to occur. Solvent, solutes, and particles smaller than the membrane pore size pass through the membrane, while particles larger than the pore size are retained, and thereby concentrated. In bioprocessing applications, concentration may be followed by diafiltration.

The term diafiltration, as used herein, refers to a dilution and re-concentration of the solution or liquid, where in order to effectively remove permeate components from the solution or liquid, fresh solvent may be added to the feed to replace the permeate volume, at the same rate as the permeate flow rate, such that the volume in the system remains constant. This is analogous to the washing of filter cake to remove soluble components.

EXAMPLES

Example 1

In order to perform an optimisation programme on the ULTRAFILTRATION of an solution containing Anti-IL-20 antibody, solution A was diafiltrated against solution B (5×retentate volume) on a Äktacrossflow equipped with a Pellicon 3, Ultracel 30 K membrane, 88 cm2 module (Millipore).

Solution A:
100 g/L Anti IL20
150 mM Sucrose
25 mMArg
25 mMNaCl
33 mM His
pH 6.5
Solution B:
25 mMArg
25 mMNaCl
33 mM His
pH 6.5

The Äktacrossflow was also equipped with a heat exchanger (Exergy, series 17 model 00402) used to regulate the retentate temperature to 45 C. Delta P (Pin-Pout) was 2 bar and TMP (Trans membrane pressure) was 1 bar. After diafiltration the retentate was concentrated with ultrafiltration according to Table 1.

The effect of diafiltration was that the appearance of the solution turned from clear to milky, indicating precipitation of the protein.

Concentration factor is a number which is reciprocal to the volume reduction of the retentate during ultrafiltration concentration. When the retentate volume is reduced to ½, the concentration factor will be 2. This factor is used to determine the calculated mAb concentration by multiplying with the original concentration: 108.3×2=216.6

During the following concentration of anti-IL20 solutions in solution B with and without 150 mM sucrose the mAb content was measured and compared to the calculated content (calculated by concentration factor), Table 1.

TABLE 1

Comparison of calculated concentration versus measured (actual) concentration, with and without addition of sucrose.

| Concentration with sucrose (Solution A) | | | Concentration without sucrose (Solution B) | | |
|---|---|---|---|---|---|
| Calculated conc.(g/L) | Measured conc.(g/L) | Concentration factor | Calculated conc.(g/L) | Measured conc.(g/L) | Concentration factor |
| 108.3 | 108.5* | 1 | 91.8 | 77.8* | 1 |
| 216.6 | 215.8 | 2 | 209.3 | 136.7 | 2.28 |
| 270.8 | 243.1 | 2.5 | 229.5 | 145.3 | 2.5 |
| 359.55 | 303.3 | 3.32 | 275.4 | 162.6 | 3 |
| | | | 325.0 | 183.7 | 3.54 |
| | | | 372.7 | 197.9 | 4.06 |

(*The fact that there is difference between measure and calculated concentrations already with a concentration factor 1 is a result of precipitation during diafiltration.)

This shows a difference in the calculated versus measured concentrations which could be explained by creation of a build-up layer of extremely concentrated protein at the membrane surface, maybe fouled or precipitated protein or protein aggregates. The difference is much larger when sucrose is not present.

Example 2

In order to investigate the effect addition of sucrose before ultrafiltration, on the formation of HMWP (High Molecular Weight Proteins: aggregates) during ultrafiltration the retentate contentment of HMWP was measured including some samples from washing of the cassette after emptying for product as can be seen the washing fractions are of substantially lower concentrations than the original retentate. The HMWP content of the wash fraction is interesting because it shows the constitution of the gel—or build up layer material which is not shown in the retentate. The overall result is that the material with sucrose present during concentration has lower content of HMWP in accordance with the theory that sucrose protects the mAb.

Content of mAb was determined by UV280 nm absorption with a NANODROP™ 2000C instrument (Thermo Scientific) and the HMWP was determined by analytical a SEC (Size Exclusion Chromatography) HPLC method with a TSK Gel G3000SWXL 7.8x300 mm column.

TABLE 2

The HMPW content and mAb concentrations of retentate and washing portions from ultrafiltration of solution B (without sucrose).

| Sample ID | Concentration (g/L) | HMWP (%) |
|---|---|---|
| Retentate | 174 | 1.2 |
| Wash 1 | 108 | 1.2 |

TABLE 2-continued

The HMPW content and mAb concentrations of retentate and washing portions from ultrafiltration of solution B (without sucrose).

| Sample ID | Concentration (g/L) | HMWP (%) |
|---|---|---|
| Wash 2 | 67 | 1.1 |
| Wash 3 | 41 | 1.1 |

TABLE 3

HMPW content and mAb concentrations of retentate and washing portions from ultrafiltration of solution A (with sucrose).

| Sample ID | Concentration (g/L) | HMWP (%) |
|---|---|---|
| Retentate | 296 | 1.0 |
| Wash 1 | 148 | 1.0 |
| Wash 2 | 95 | 1.0 |
| Wash 3 | 59 | 0.9 |
| Wash 4 | 26 | 0.9 |

It may be concluded from both Table 1. and Tables 2. and 3. that the improved correlation between measured and calculated retentate concentrations during ultrafiltration concentration of solution A and the results from HMWP analysis indicate that the presence of sucrose prevents to some extent the aggregation of the protein and the creation of build-up layer (or fouling).

Example 3

In order to investigate the effect addition of sucrose before ultrafiltration, on the protein recovery or yield of the process, the concentration of mAb was measured in the retentate and samples from washing of the cassette after emptying for product.

Content of mAb was determined by UV280 nm absorption with a NANODROP™ 2000C instrument (Thermo Scientific).

Table 4. shows the yield or recovery of the anti-IL-20 antibody from solution B retentate and samples of the cassette. The starting volume was 140 ml, with an antibody concentration of 107.45 g/L, or in total 15 g of antibody.

TABLE 4

Yield of antibody inretentate and washing portions from ultrafiltration of solution B (without sucrose).

| Sample ID | Volume (ml) | Concentration (g/L) | mAb (g) |
|---|---|---|---|
| Retentate | 37.5 | 192.2 | 7.2 |
| Wash 1 | 22 | 118.9 | 2.6 |
| Wash 2 | 24 | 82.1 | 2.0 |
| Wash 3 | 50 | 48.3 | 2.2 |
| Total | | | 14.0 |
| Total yield | | | 93.0% |

Table 5. shows the yield or recovery of anti-IL-20 from solution A. The starting volume was 300 ml, with an antibody concentration of 107.45 g/L or 32.2 g of antibody in total.

TABLE 5

Yield of antibody inretentate and washing portions from ultrafiltration of solution A (with sucrose).

| Sample ID | Volume (ml) | Concentration (g/L) | mAb (g) |
|---|---|---|---|
| Retentate | 68 | 303.28 | 20.6 |
| Wash 1 | 24 | 90 | 2.2 |
| Wash 2 | 23 | 171.1 | 3.9 |
| Wash 3 | 23 | 105.5 | 2.4 |
| Wash 4 | 23 | 66 | 1.5 |
| Wash 5 | 50 | 29.8 | 1.5 |
| Total | | | 32.2 |
| Total yield | | | 99.8% |

The following is a non-limiting list of embodiments of the present invention.

1. A method of ultrafiltration of a highly concentrated protein solution, wherein sucrose is added to the solution when the protein concentration of the solution is between 40 and 60 g/L before further concentration by ultrafiltration.

2. A method of decreasing the difference between a calculated or estimated protein concentration and actual measured protein concentration in a highly concentrated protein ultrafiltration retentate, wherein sucrose is added to the solution when the protein concentration of the solution is between 40 g/L and 60 g/L before further concentration by ultrafiltration.

3. A method of decreasing the difference between a calculated or estimated protein concentration and an actual measured protein concentration in a highly concentrated protein ultrafiltration retentate to less than 15%, wherein sucrose is added to the solution when the protein concentration of the solution is between 40 and 60 g/L before further concentration by ultrafiltration.

4. A method of decreasing the difference between a calculated or estimated protein concentration and an actual measured protein concentration in a highly concentrated protein ultrafiltration retentate to less than 20%, wherein sucrose is added to the solution when the protein concentration of the solution is between 40 and 60 g/L before further concentration by ultrafiltration.

5. A method of decreasing the difference between a calculated protein or estimated concentration and an actual measured protein concentration in a highly concentrated protein ultrafiltration retentate to less than 25%, wherein sucrose is added to the solution when the protein concentration of the solution is between 40 and 60 g/L before further concentration by ultrafiltration.

6. A method of decreasing the difference between a calculated or estimated protein concentration and an actual measured protein concentration in a highly concentrated protein ultrafiltration to less than 30%, wherein sucrose is added to the solution when the protein concentration of the solution is between 40 and 60 g/L before further concentration by ultrafiltration.

7. A method of ultrafiltration of a highly concentrated protein solution, where the difference between the calculated or estimated protein concentration and the actual measured protein concentration in the highly concentrated ultrafiltration retentate is less than 15%, wherein sucrose is added to the solution when the protein concentration of the solution is between 40 and 60 g/L before further concentration by ultrafiltration.

8. A method of ultrafiltration of a highly concentrated protein solution, where the difference between the calculated or estimated protein concentration and the actual measured protein concentration in the highly concentrated ultrafiltration retentate is less than 20%, wherein sucrose is added to the solution when the protein concentration of the solution is between 40 and 60 g/L before further concentration by ultrafiltration.

9. A method of ultrafiltration of a highly concentrated protein solution, where the difference between the calculated or estimated protein concentration and the actual measured protein concentration in the highly concentrated ultrafiltration retentate is less than 25%, wherein sucrose is added to the solution when the protein concentration of the solution is between 40 and 60 g/L before further concentration by ultrafiltration.

10. A method of ultrafiltration of a highly concentrated protein solution, where the difference between the calculated or estimated protein concentration and the actual measured protein concentration in the highly concentrated ultrafiltration retentate is less than 30%, wherein sucrose is added to the solution when the protein concentration of the solution is between 40 and 60 g/L before further concentration by ultrafiltration.

11. A method of increasing the recovery of protein by ultrafiltration of a highly concentrated protein solution, wherein sucrose is added to the solution when the protein concentration of the solution is between 40 and 60 g/L before further concentration by ultrafiltration.

12. A method of increasing the recovery of protein by ultrafiltration of a highly concentrated protein solution to above 94% of the total amount of said protein in the solution to be ultrafiltrated, wherein sucrose is added to the solution when the protein concentration of the solution is between 40 and 60 g/L before further concentration by ultrafiltration.

13. A method of increasing the recovery of protein by ultrafiltration of a highly concentrated protein solution to above 95% of the total amount of said protein in the solution to be ultrafiltrated, wherein sucrose is added to the solution when the protein concentration of the solution is between 40 and 60 g/L before further concentration by ultrafiltration.

14. A method of increasing the recovery of protein by ultrafiltration of a highly concentrated protein solution to above 96% of the total amount of said protein in the solution to be ultrafiltrated, wherein sucrose is added to the solution when the protein concentration of the solution is between 40 and 60 g/L before further concentration by ultrafiltration.

15. A method of increasing the recovery of protein by ultrafiltration of a highly concentrated protein solution to above 97% of the total amount of said protein in the solution to be ultrafiltrated, wherein sucrose is added to the solution when the protein concentration of the solution is between 40 and 60 g/L before further concentration by ultrafiltration.

16. A method of increasing the recovery of protein by ultrafiltration of a highly concentrated protein solution to above 98% of the total amount of said protein in the solution to be ultrafiltrated, wherein sucrose is added to the solution when the protein concentration of the solution is between 40 and 60 g/L before further concentration by ultrafiltration.

17. A method of increasing the recovery of protein by ultrafiltration of a highly concentrated protein solution to above 99% of the total amount of said protein in the solution to be ultrafiltrated, wherein sucrose is added to the solution when the protein concentration of the solution is between 40 and 60 g/L before further concentration by ultrafiltration.

18. A method of ultrafiltration of a highly concentrated protein solution, where the recovery of protein by ultrafiltration is above 95% of the total amount of said protein in the solution to be ultrafiltrated, wherein sucrose is added to the solution when the protein concentration of the solution is between 40 and 60 g/L before further concentration by ultrafiltration.

19. A method of ultrafiltration of a highly concentrated protein solution, where the recovery of protein by ultrafiltration is above 96% of the total amount of said protein in the solution to be ultrafiltrated, wherein sucrose is added to the solution when the protein concentration of the solution is between 40 and 60 g/L before further concentration by ultrafiltration.

20. A method of ultrafiltration of a highly concentrated protein solution, where the recovery of protein by ultrafiltration is above 97% of the total amount of said protein in the solution to be ultrafiltrated, wherein sucrose is added to the solution when the protein concentration of the solution is between 40 and 60 g/L before further concentration by ultrafiltration.

21. A method of ultrafiltration of a highly concentrated protein solution, where the recovery of protein by ultrafiltration is above 98% of the total amount of said protein in the solution to be ultrafiltrated, wherein sucrose is added to the solution when the protein concentration of the solution is between 40 and 60 g/L before further concentration by ultrafiltration.

22. A method of ultrafiltration of a highly concentrated protein solution, where the recovery of protein by ultrafiltration is above 99% of the total amount of said protein in the solution to be ultrafiltrated, wherein sucrose is added to the solution when the protein concentration of the solution is between 40 and 60 g/L before further concentration by ultrafiltration.

23. A method of increasing the recovery of protein by ultrafiltration of a highly concentrated protein solution in the final ultrafiltration retentate to above 50% of the total amount of said protein in the solution to be ultrafiltrated, wherein sucrose is added to the solution when the protein concentration of the solution is between 40 and 60 g/L before further concentration by ultrafiltration.

24. A method of increasing the recovery of protein by ultrafiltration of a highly concentrated protein solution in the final ultrafiltration retentate to above 55% of the total amount of said protein in the solution to be ultrafiltrated, wherein sucrose is added to the solution when the protein concentration of the solution is between 40 and 60 g/L before further concentration by ultrafiltration.

25. A method of increasing the recovery of protein by ultrafiltration of a highly concentrated protein solution in the final ultrafiltration retentate to above 60% of the total amount of said protein in the solution to be ultrafiltrated, wherein sucrose is added to the solution when the protein concentration of the solution is between 40 and 60 g/L before further concentration by ultrafiltration.

26. A method of ultrafiltration of a highly concentrated protein solution, where the recovery of protein by ultrafiltration in the final ultrafiltration retentate is above 50% of the total amount of said protein in the solution to be ultrafiltrated, wherein sucrose is added to the solution when the protein concentration of the solution is between 40 and 60 g/L before further concentration by ultrafiltration.

27. A method of ultrafiltration of a highly concentrated protein solution, where the recovery of protein by ultrafiltration in the final ultrafiltration retentate is above 55% of the total amount of said protein in the solution to be ultrafiltrated, wherein sucrose is added to the solution when the protein concentration of the solution is between 40 and 60 g/L before further concentration by ultrafiltration.

28. A method of ultrafiltration of a highly concentrated protein solution, where the recovery of protein by ultrafiltration in the final ultrafiltration retentate is above 60% of the total amount of said protein in the solution to be ultrafiltrated, wherein sucrose is added to the solution when the protein concentration of the solution is between 40 and 60 g/L before further concentration by ultrafiltration.

29. A method of stabilizing a highly concentrated protein solution during ultrafiltration, wherein sucrose is added to the solution when the protein concentration of the solution is between 40 and 60 g/L before further concentration by ultrafiltration.

30. A method of stabilizing a highly concentrated protein solution during ultrafiltration, where the level of HMWP aggregates is 1% or below 1%, wherein sucrose is added to the solution when the protein concentration of the solution is between 40 and 60 g/L before further concentration by ultrafiltration.

31. A method of stabilizing a highly concentrated protein solution during ultrafiltration, where the level of HMWP aggregates is below 1.1%, wherein sucrose is added to the solution when the protein concentration of the solution is between 40 and 60 g/L before further concentration by ultrafiltration.

32. A method of decreasing the formation of HWMP aggregates in a highly concentrated protein solution during ultrafiltration, wherein sucrose is added to the solution when the protein concentration of the solution is between 40 and 60 g/L before further concentration by ultrafiltration.

33. A method of decreasing the formation of HWMP aggregates in a highly concentrated protein solution during ultrafiltration to 1% or below 1%, wherein sucrose is added to the solution when the protein concentration of the solution is between 40 and 60 g/L before further concentration by ultrafiltration.

34. A method of decreasing the formation of HWMP aggregates in a highly concentrated protein solution during ultrafiltration to below 1.1%, wherein sucrose is added to the solution when the protein concentration of the solution is between 40 and 60 g/L before further concentration by ultrafiltration.

35. A method of ultrafiltration of a highly concentrated protein solution, where the level of HMWP aggregates is kept at 1% or below 1%, wherein sucrose is added to the solution when the protein concentration of the solution is between 40 and 60 g/L before further concentration by ultrafiltration.

36. A method of ultrafiltration of a highly concentrated protein solution, where the level of HMWP aggregates is kept below 1.1%, wherein sucrose is added to the solution when the protein concentration of the solution is between 40 and 60 g/L before further concentration by ultrafiltration.

37. A method of stabilizing a highly concentrated protein solution during ultrafiltration, where the formation of HMWP aggregates during ultrafiltration is decreased by 10%, wherein sucrose is added to the solution when the protein concentration of the solution is between 40 and 60 g/L before further concentration by ultrafiltration.

38. A method of stabilizing a highly concentrated protein solution during ultrafiltration, where the formation of HMWP aggregates during ultrafiltration is decreased by 20%, wherein sucrose is added to the solution when the protein concentration of the solution is between 40 and 60 g/L before further concentration by ultrafiltration.

39. A method of ultrafiltration of a highly concentrated protein solution, where the formation of HMWP aggregates is decreased by 10%, wherein sucrose is added to the solution when the protein concentration of the solution is between 40 and 60 g/L before further concentration by ultrafiltration.

40. A method of ultrafiltration of a highly concentrated protein solution, where the formation of HMWP aggregates is decreased by 20%, wherein sucrose is added to the solution when the protein concentration of the solution is between 40 and 60 g/L before further concentration by ultrafiltration.

41. A method according to any of embodiments 1-40, wherein the protein concentration is 40 g/L when sucrose is added to the solution.

42. A method according to any of embodiments 1-40, wherein the protein concentration is 41 g/L when sucrose is added to the solution.

43. A method according to any of embodiments 1-40, wherein the protein concentration is 42 g/L when sucrose is added to the solution.

44. A method according to any of embodiments 1-40, wherein the protein concentration is 43 g/L when sucrose is added to the solution.

45. A method according to any of embodiments 1-40, wherein the protein concentration is 44 g/L when sucrose is added to the solution.

46. A method according to any of embodiments 1-40, wherein the protein concentration is 45 g/L when sucrose is added to the solution.

47. A method according to any of embodiments 1-40, wherein the protein concentration is 46 g/L when sucrose is added to the solution.

48. A method according to any of embodiments 1-40, wherein the protein concentration is 47 g/L when sucrose is added to the solution.

49. A method according to any of embodiments 1-40, wherein the protein concentration is 48 g/L when sucrose is added to the solution.

50. A method according to any of embodiments 1-40, wherein the protein concentration is 49 g/L when sucrose is added to the solution.

51. A method according to any of embodiments 1-40, wherein the protein concentration is 50 g/L when sucrose is added to the solution.

52. A method according to any of embodiments 1-40, wherein the protein concentration is 51 g/L when sucrose is added to the solution.

53. A method according to any of embodiments 1-40, wherein the protein concentration is 52 g/L when sucrose is added to the solution.

54. A method according to any of embodiments 1-40, wherein the protein concentration is 53 g/L when sucrose is added to the solution.

55. A method according to any of embodiments 1-40, wherein the protein concentration is 54 g/L when sucrose is added to the solution.

56. A method according to any of embodiments 1-40, wherein the protein concentration is 55 g/L when sucrose is added to the solution.

57. A method according to any of embodiments 1-40, wherein the protein concentration is 56 g/L when sucrose is added to the solution.

58. A method according to any of embodiments 1-40, wherein the protein concentration is 57 g/L when sucrose is added to the solution.

59. A method according to any of embodiments 1-40, wherein the protein concentration is 58 g/L when sucrose is added to the solution.

60. A method according to any of embodiments 1-40, wherein the protein concentration is 59 g/L when sucrose is added to the solution.

61. A method according to any of embodiments 1-40, wherein the protein concentration is 60 g/L when sucrose is added to the solution.

62. A method according to any of embodiments 1-40, wherein the protein concentration is between 40 g/L and 45 g/L when sucrose is added to the solution.

63. A method according to any of embodiments 1-40, wherein the protein concentration is between 40 g/L and 50 g/L when sucrose is added to the solution.

64. A method according to any of embodiments 1-40, wherein the protein concentration is between 45 g/L and 50 g/L when sucrose is added to the solution.

65. A method according to any of embodiments 1-40, wherein the protein concentration is between 45 g/L and 55 g/L when sucrose is added to the solution.

66. A method according to any of embodiments 1-40, wherein the protein concentration is between 50 g/L and 55 g/L when sucrose is added to the solution.

67. A method according to any of embodiments 1-40, wherein the protein concentration is between 50 g/L and 60 g/L when sucrose is added to the solution.

68. A method according to any of embodiments 1-40, wherein the protein concentration is between 55 g/L and 60 g/L when sucrose is added to the solution.

69. A method according to any of embodiments 1-68, wherein the sucrose is added in the concentration of between 50 mM and 300 mM.

70. A method according to any of embodiments 1-68, wherein the sucrose is added in the concentration of between 50 mM and 250 mM.

71. A method according to any of embodiments 1-68, wherein the sucrose is added in the concentration of between 50 mM and 200 mM.

72. A method according to any of embodiments 1-68, wherein the sucrose is added in the concentration of between 50 mM and 150 mM.

73. A method according to any of embodiments 1-68, wherein the sucrose is added in the concentration of between 50 mM and 100 mM.

74. A method according to any of embodiments 1-68, wherein the sucrose is added in the concentration of between 100 mM and 300 mM.

75. A method according to any of embodiments 1-68, wherein the sucrose is added in the concentration of between 100 mM and 250 mM.

76. A method according to any of embodiments 1-68, wherein the sucrose is added in the concentration of between 100 mM and 200 mM.

77. A method according to any of embodiments 1-68, wherein the sucrose is added in the concentration of between 100 mM and 150 mM.

78. A method according to any of embodiments 1-68, wherein the sucrose is added in the concentration of 100 mM.

79. A method according to any of embodiments 1-68, wherein the sucrose is added in the concentration of 110 mM.

80. A method according to any of embodiments 1-68, wherein the sucrose is added in the concentration of 120 mM.

81. A method according to any of embodiments 1-68, wherein the sucrose is added in the concentration of 130 mM.

82. A method according to any of embodiments 1-68, wherein the sucrose is added in the concentration of 140 mM.

83. A method according to any of embodiments 1-68, wherein the sucrose is added in the concentration of 150 mM.

84. A method according to any of embodiments 1-68, wherein the sucrose is added in the concentration of 160 mM.

85. A method according to any of embodiments 1-68, wherein the sucrose is added in the concentration of 175 mM.

86. A method according to any of embodiments 1-68, wherein the sucrose is added in the concentration of 200 mM.

87. A method according to any of embodiments 1-68, wherein the sucrose is added in the concentration of 225 mM.

88. A method according to any of embodiments 1-68, wherein the sucrose is added in the concentration of 250 mM.

89. A method according to any of embodiments 1-68, wherein the sucrose is added in the concentration of 300 mM.

90. A method of ultrafiltration of a highly concentrated antibody solution, wherein sucrose is added to the solution when the antibody concentration of the solution is between 40 and 60 g/L before further concentration by ultrafiltration.

91. A method of decreasing the difference between a calculated or estimated antibody concentration and actual measured antibody concentration in a highly concentrated antibody ultrafiltration retentate, wherein sucrose is added to the solution when the antibody concentration of the solution is between 40 g/L and 60 g/L before further concentration by ultrafiltration.

92. A method of decreasing the difference between a calculated or estimated antibody concentration and an actual measured antibody concentration in a highly concentrated antibody ultrafiltration retentate to less than 15%, wherein sucrose is added to the solution when the antibody concentration of the solution is between 40 and 60 g/L before further concentration by ultrafiltration.

93. A method of decreasing the difference between a calculated or estimated antibody concentration and an actual measured antibody concentration in a highly concentrated antibody ultrafiltration retentate to less than 20%, wherein sucrose is added to the solution when the antibody concentration of the solution is between 40 and 60 g/L before further concentration by ultrafiltration.

94. A method of decreasing the difference between a calculated antibody or estimated concentration and an actual measured antibody concentration in a highly concentrated antibody ultrafiltration retentate to less than 25%, wherein sucrose is added to the solution when the antibody concentration of the solution is between 40 and 60 g/L before further concentration by ultrafiltration.

95. A method of decreasing the difference between a calculated or estimated antibody concentration and an actual measured antibody concentration in a highly concentrated antibody ultrafiltration to less than 30%, wherein sucrose is added to the solution when the antibody concentration of the solution is between 40 and 60 g/L before further concentration by ultrafiltration.

96. A method of ultrafiltration of a highly concentrated antibody solution, where the difference between the calculated or estimated antibody concentration and the actual measured antibody concentration in the highly concentrated ultrafiltration retentate is less than 15%, wherein sucrose is added to the solution when the antibody concentration of the solution is between 40 and 60 g/L before further concentration by ultrafiltration.

97. A method of ultrafiltration of a highly concentrated antibody solution, where the difference between the calculated or estimated antibody concentration and the actual measured antibody concentration in the highly concentrated ultrafiltration retentate is less than 20%, wherein sucrose is added to the solution when the antibody concentration of the solution is between 40 and 60 g/L before further concentration by ultrafiltration.

98. A method of ultrafiltration of a highly concentrated antibody solution, where the difference between the calculated or estimated antibody concentration and the actual measured antibody concentration in the highly concentrated ultrafiltration retentate is less than 25%, wherein sucrose is added to the solution when the antibody concentration of the solution is between 40 and 60 g/L before further concentration by ultrafiltration.

99. A method of ultrafiltration of a highly concentrated antibody solution, where the difference between the calculated or estimated antibody concentration and the actual measured antibody concentration in the highly concentrated ultrafiltration retentate is less than 30%, wherein sucrose is added to the solution when the antibody concentration of the solution is between 40 and 60 g/L before further concentration by ultrafiltration.

100. A method of increasing the recovery of antibody by ultrafiltration of a highly concentrated antibody solution, wherein sucrose is added to the solution when the antibody concentration of the solution is between 40 and 60 g/L before further concentration by ultrafiltration.

101. A method of increasing the recovery of antibody by ultrafiltration of a highly concentrated antibody solution to above 94% of the total amount of said antibody in the solution to be ultrafiltrated, wherein sucrose is added to the solution when the antibody concentration of the solution is between 40 and 60 g/L before further concentration by ultrafiltration.

102. A method of increasing the recovery of antibody by ultrafiltration of a highly concentrated antibody solution to above 95% of the total amount of said antibody in the solution to be ultrafiltrated, wherein sucrose is added to the solution when the antibody concentration of the solution is between 40 and 60 g/L before further concentration by ultrafiltration.

103. A method of increasing the recovery of antibody by ultrafiltration of a highly concentrated antibody solution to above 96% of the total amount of said antibody in the solution to be ultrafiltrated, wherein sucrose is added to the solution when the antibody concentration of the solution is between 40 and 60 g/L before further concentration by ultrafiltration.

104. A method of increasing the recovery of antibody by ultrafiltration of a highly concentrated antibody solution to above 97% of the total amount of said antibody in the solution to be ultrafiltrated, wherein sucrose is added to the solution when the antibody concentration of the solution is between 40 and 60 g/L before further concentration by ultrafiltration.

105. A method of increasing the recovery of antibody by ultrafiltration of a highly concentrated antibody solution to above 98% of the total amount of said antibody in the solution to be ultrafiltrated, wherein sucrose is added to the solution when the antibody concentration of the solution is between 40 and 60 g/L before further concentration by ultrafiltration.

106. A method of increasing the recovery of antibody by ultrafiltration of a highly concentrated antibody solution to above 99% of the total amount of said antibody in the solution to be ultrafiltrated, wherein sucrose is added to the solution when the antibody concentration of the solution is between 40 and 60 g/L before further concentration by ultrafiltration.

107. A method of ultrafiltration of a highly concentrated antibody solution, where the recovery of antibody by ultrafiltration is above 95% of the total amount of said antibody in the solution to be ultrafiltrated, wherein sucrose is added to the solution when the antibody concentration of the solution is between 40 and 60 g/L before further concentration by ultrafiltration.

107. A method of ultrafiltration of a highly concentrated antibody solution, where the recovery of antibody by ultrafiltration is above 96% of the total amount of said antibody in the solution to be ultrafiltrated, wherein sucrose is added to the solution when the antibody concentration of the solution is between 40 and 60 g/L before further concentration by ultrafiltration.

109. A method of ultrafiltration of a highly concentrated antibody solution, where the recovery of antibody by ultrafiltration is above 97% of the total amount of said antibody in the solution to be ultrafiltrated, wherein sucrose is added to the solution when the antibody concentration of the solution is between 40 and 60 g/L before further concentration by ultrafiltration.

110. A method of ultrafiltration of a highly concentrated antibody solution, where the recovery of antibody by ultrafiltration is above 98% of the total amount of said antibody in the solution to be ultrafiltrated, wherein sucrose is added to the solution when the antibody concentration of the solution is between 40 and 60 g/L before further concentration by ultrafiltration.

111. A method of ultrafiltration of a highly concentrated antibody solution, where the recovery of antibody by ultrafiltration is above 99% of the total amount of said antibody in the solution to be ultrafiltrated, wherein sucrose is added to the solution when the antibody concentration of the solution is between 40 and 60 g/L before further concentration by ultrafiltration.

112. A method of increasing the recovery of antibody by ultrafiltration of a highly concentrated antibody solution in the final ultrafiltration retentate to above 50% of the total amount of said antibody in the solution to be ultrafiltrated, wherein sucrose is added to the solution when the antibody concentration of the solution is between 40 and 60 g/L before further concentration by ultrafiltration.

113. A method of increasing the recovery of antibody by ultrafiltration of a highly concentrated antibody solution in the final ultrafiltration retentate to above 55% of the total amount of said antibody in the solution to be ultrafiltrated, wherein sucrose is added to the solution when the antibody concentration of the solution is between 40 and 60 g/L before further concentration by ultrafiltration.

114. A method of increasing the recovery of antibody by ultrafiltration of a highly concentrated antibody solution in the final ultrafiltration retentate to above 60% of the total amount of said antibody in the solution to be ultrafiltrated, wherein sucrose is added to the solution when the antibody concentration of the solution is between 40 and 60 g/L before further concentration by ultrafiltration.

115. A method of ultrafiltration of a highly concentrated antibody solution, where the recovery of antibody by ultrafiltration in the final ultrafiltration retentate is above 50% of the total amount of said antibody in the solution to be ultrafiltrated, wherein sucrose is added to the solution when the antibody concentration of the solution is between 40 and 60 g/L before further concentration by ultrafiltration.

116. A method of ultrafiltration of a highly concentrated antibody solution, where the recovery of antibody by ultrafiltration in the final ultrafiltration retentate is above 55% of the total amount of said antibody in the solution to be ultrafiltrated, wherein sucrose is added to the solution when the antibody concentration of the solution is between 40 and 60 g/L before further concentration by ultrafiltration.

117. A method of ultrafiltration of a highly concentrated antibody solution, where the recovery of antibody by ultrafiltration in the final ultrafiltration retentate is above 60% of the total amount of said antibody in the solution to be ultrafiltrated, wherein sucrose is added to the solution when the antibody concentration of the solution is between 40 and 60 g/L before further concentration by ultrafiltration.

118. A method of stabilizing a highly concentrated antibody solution during ultrafiltration, wherein sucrose is added to the solution when the antibody concentration of the solution is between 40 and 60 g/L before further concentration by ultrafiltration.

119. A method of stabilizing a highly concentrated antibody solution during ultrafiltration, where the level of HMWP aggregates is 1% or below 1%, wherein sucrose is added to the solution when the antibody concentration of the solution is between 40 and 60 g/L before further concentration by ultrafiltration.

120. A method of stabilizing a highly concentrated antibody solution during ultrafiltration, where the level of HMWP aggregates is below 1.1%, wherein sucrose is added to the solution when the antibody concentration of the solution is between 40 and 60 g/L before further concentration by ultrafiltration.

121. A method of decreasing the formation of HWMP aggregates in a highly concentrated antibody solution during ultrafiltration, wherein sucrose is added to the solution when the antibody concentration of the solution is between 40 and 60 g/L before further concentration by ultrafiltration.

122. A method of decreasing the formation of HWMP aggregates in a highly concentrated antibody solution during ultrafiltration to 1% or below 1%, wherein sucrose is added to the solution when the antibody concentration of the solution is between 40 and 60 g/L before further concentration by ultrafiltration.

123. A method of decreasing the formation of HWMP aggregates in a highly concentrated antibody solution during ultrafiltration to below 1.1%, wherein sucrose is added to the solution when the antibody concentration of the solution is between 40 and 60 g/L before further concentration by ultrafiltration.

124. A method of ultrafiltration of a highly concentrated antibody solution, where the level of HMWP aggregates is kept at 1% or below 1%, wherein sucrose is added to the solution when the antibody concentration of the solution is between 40 and 60 g/L before further concentration by ultrafiltration.

125. A method of ultrafiltration of a highly concentrated antibody solution, where the level of HMWP aggregates is kept below 1.1%, wherein sucrose is added to the solution when the antibody concentration of the solution is between 40 and 60 g/L before further concentration by ultrafiltration.

126. A method of stabilizing a highly concentrated antibody solution during ultrafiltration, where the formation of HMWP aggregates during ultrafiltration is decreased by 10%, wherein sucrose is added to the solution when the antibody concentration of the solution is between 40 and 60 g/L before further concentration by ultrafiltration.

127. A method of stabilizing a highly concentrated antibody solution during ultrafiltration, where the formation of HMWP aggregates during ultrafiltration is decreased by 20%, wherein sucrose is added to the solution when the antibody concentration of the solution is between 40 and 60 g/L before further concentration by ultrafiltration.

128. A method of ultrafiltration of a highly concentrated antibody solution, where the formation of HMWP aggregates is decreased by 10%, wherein sucrose is added to the solution when the antibody concentration of the solution is between 40 and 60 g/L before further concentration by ultrafiltration.

129. A method of ultrafiltration of a highly concentrated antibody solution, where the formation of HMWP aggregates is decreased by 20%, wherein sucrose is added to the solution when the antibody concentration of the solution is between 40 and 60 g/L before further concentration by ultrafiltration.

130. A method according to any of embodiments 90-129, wherein the antibody concentration is 40 g/L when sucrose is added to the solution.

131. A method according to any of embodiments 90-129, wherein the antibody concentration is 41 g/L when sucrose is added to the solution.

132. A method according to any of embodiments 90-129, wherein the antibody concentration is 42 g/L when sucrose is added to the solution.

133. A method according to any of embodiments 90-129, wherein the antibody concentration is 43 g/L when sucrose is added to the solution.

134. A method according to any of embodiments 90-129, wherein the antibody concentration is 44 g/L when sucrose is added to the solution.

135. A method according to any of embodiments 90-129, wherein the antibody concentration is 45 g/L when sucrose is added to the solution.

136. A method according to any of embodiments 90-129, wherein the antibody concentration is 46 g/L when sucrose is added to the solution.

137. A method according to any of embodiments 90-129, wherein the antibody concentration is 47 g/L when sucrose is added to the solution.

138. A method according to any of embodiments 90-129, wherein the antibody concentration is 48 g/L when sucrose is added to the solution.

139. A method according to any of embodiments 90-129, wherein the antibody concentration is 49 g/L when sucrose is added to the solution.

140. A method according to any of embodiments 90-129, wherein the antibody concentration is 50 g/L when sucrose is added to the solution.

141. A method according to any of embodiments 90-129, wherein the antibody concentration is 51 g/L when sucrose is added to the solution.

142. A method according to any of embodiments 90-129, wherein the antibody concentration is 52 g/L when sucrose is added to the solution.

143. A method according to any of embodiments 90-129, wherein the antibody concentration is 53 g/L when sucrose is added to the solution.

144. A method according to any of embodiments 90-129, wherein the antibody concentration is 54 g/L when sucrose is added to the solution.

145. A method according to any of embodiments 90-129, wherein the antibody concentration is 55 g/L when sucrose is added to the solution.

146. A method according to any of embodiments 90-129, wherein the antibody concentration is 56 g/L when sucrose is added to the solution.

147. A method according to any of embodiments 90-129, wherein the antibody concentration is 57 g/L when sucrose is added to the solution.

148. A method according to any of embodiments 90-129, wherein the antibody concentration is 58 g/L when sucrose is added to the solution.

149. A method according to any of embodiments 90-129, wherein the antibody concentration is 59 g/L when sucrose is added to the solution.

150. A method according to any of embodiments 90-129, wherein the antibody concentration is 60 g/L when sucrose is added to the solution.

151. A method according to any of embodiments 90-129, wherein the antibody concentration is between 40 g/L and 45 g/L when sucrose is added to the solution.

152. A method according to any of embodiments 90-129, wherein the antibody concentration is between 40 g/L and 50 g/L when sucrose is added to the solution.

153. A method according to any of embodiments 90-129, wherein the antibody concentration is between 45 g/L and 50 g/L when sucrose is added to the solution.

154. A method according to any of embodiments 90-129, wherein the antibody concentration is between 45 g/L and 55 g/L when sucrose is added to the solution.

155. A method according to any of embodiments 90-129, wherein the antibody concentration is between 50 g/L and 55 g/L when sucrose is added to the solution.

156. A method according to any of embodiments 90-129, wherein the antibody concentration is between 50 g/L and 60 g/L when sucrose is added to the solution.

157. A method according to any of embodiments 90-129, wherein the antibody concentration is between 55 g/L and 60 g/L when sucrose is added to the solution.

158. A method according to any of embodiments 90-157, wherein the sucrose is added in the concentration of between 50 mM and 300 mM.

159. A method according to any of embodiments 90-157, wherein the sucrose is added in the concentration of between 50 mM and 250 mM.

160. A method according to any of embodiments 90-157, wherein the sucrose is added in the concentration of between 50 mM and 200 mM.

161. A method according to any of embodiments 90-157, wherein the sucrose is added in the concentration of between 50 mM and 150 mM.

162. A method according to any of embodiments 90-157, wherein the sucrose is added in the concentration of between 50 mM and 100 mM.

163. A method according to any of embodiments 90-157, wherein the sucrose is added in the concentration of between 100 mM and 300 mM.

164. A method according to any of embodiments 90-157, wherein the sucrose is added in the concentration of between 100 mM and 250 mM.

165. A method according to any of embodiments 90-157, wherein the sucrose is added in the concentration of between 100 mM and 200 mM.

166. A method according to any of embodiments 90-157, wherein the sucrose is added in the concentration of between 100 mM and 150 mM.

167. A method according to any of embodiments 90-157, wherein the sucrose is added in the concentration of 100 mM.

168. A method according to any of embodiments 90-157, wherein the sucrose is added in the concentration of 110 mM.

169. A method according to any of embodiments 90-157, wherein the sucrose is added in the concentration of 120 mM.

170. A method according to any of embodiments 90-157, wherein the sucrose is added in the concentration of 130 mM.

171. A method according to any of embodiments 90-157, wherein the sucrose is added in the concentration of 140 mM.

172. A method according to any of embodiments 90-157, wherein the sucrose is added in the concentration of 150 mM.

173. A method according to any of embodiments 90-157, wherein the sucrose is added in the concentration of 160 mM.

174. A method according to any of embodiments 90-157, wherein the sucrose is added in the concentration of 175 mM.

175. A method according to any of embodiments 90-157, wherein the sucrose is added in the concentration of 200 mM.

176. A method according to any of embodiments 90-157, wherein the sucrose is added in the concentration of 225 mM.

177. A method according to any of embodiments 90-157, wherein the sucrose is added in the concentration of 250 mM.

178. A method according to any of embodiments 90-157, wherein the sucrose is added in the concentration of 300 mM.

179. A method according to any of embodiments 90-178, wherein the antibody is a monoclonal antibody.

180. A method according to any of embodiments 90-179, wherein the antibody is of the IgG4 subtype.

181. A method according to any of embodiments 90-180, wherein the antibody is a human antibody.

182. A method according to any of embodiments 90-180, wherein the antibody is a humanized antibody.

183. A method according to any of embodiments 90-182, wherein the antibody is an anti-IL-20 monoclonal antibody.

184. A method of concentrating a protein in a protein solution according to any of embodiments 1-89, for use in a pharmaceutical composition.

185. A method of concentrating a protein in a protein solution according to any of embodiments 1-89, for use for manufacture of a medicament.

186. A method of treating an inflammatory disease which comprises administering to a patient the pharmaceutical composition of embodiment 184.

187. A method of treating an inflammatory disease which comprises administering to a patient the medicament of embodiment 185.

188. A method of concentrating an antibody in an antibody solution according to any of embodiments 90-183, for use in a pharmaceutical composition.

189. A method of concentrating an antibody in an antibody solution according to any of embodiments 90-183, for use for manufacture of a medicament.

190. A method of treating an inflammatory disease which comprises administering to a patient the pharmaceutical composition of embodiment 188.

191. A method of treating an inflammatory disease which comprises administering to a patient the medicament of embodiment 189.

192. A method of concentrating a highly concentrated protein solution which comprises:
(a) adding sucrose to the highly concentrated protein solution when the protein concentration is between 40 g/L and 60 g/L;
(b) concentrate the highly concentrated protein solution by ultrafiltration.

193. A method of decreasing the difference between a calculated and measured protein concentration in a highly concentrated protein ultrafiltration retentate which comprises:
(a) adding sucrose to the highly concentrated protein solution when the protein concentration is between 40 g/L and 60 g/L;
(b) concentrate the highly concentrated protein solution by ultrafiltration.

194: A method of decreasing the difference between a calculated and measured protein concentration in a highly concentrated protein ultrafiltration retentate which comprises:
(a) adding sucrose to a highly concentrated protein solution when the protein concentration is between 40 g/L and 60 g/L
(b) concentrate the highly concentrated protein solution by ultrafiltration.

195: A method of decreasing the difference between a calculated and measured protein concentration to less than 30% in a highly concentrated protein ultrafiltration retentate which comprises:
(a) adding sucrose to a highly concentrated protein solution when the protein concentration is between 40 g/L and 60 g/L
(b) concentrate the highly concentrated protein solution by ultrafiltration.

196. A method of increasing the recovery of protein by ultrafiltration of a highly concentrated protein solution which comprises:
(a) adding sucrose to the highly concentrated protein solution when the protein concentration is between 40 g/L and 60 g/L
(b) concentrate the highly concentrated protein solution by ultrafiltration.

197. A method of increasing the recovery of protein by ultrafiltration of a highly concentrated protein solution to above 50% of the total amount of said protein in the highly concentrated solution to be ultrafiltrated which comprises:
(a) adding sucrose to the highly concentrated protein solution when the protein concentration is between 40 g/L and 60 g/L
(b) concentrate the highly concentrated protein solution by ultrafiltration.

198. A method of stabilizing a highly concentrated protein solution during ultrafiltration which comprises:
(a) adding sucrose to the highly concentrated protein solution when the protein concentration is between 40 g/L and 60 g/L
(b) concentrate the highly concentrated protein solution by ultrafiltration.

199. A method of suppressing the formation of HMWP during ultrafiltration of a highly concentrated protein solution which comprises:

(a) adding sucrose to the highly concentrated protein solution when the protein concentration is between 40 g/L and 60 g/L (b) concentrate the highly concentrated protein solution by ultrafiltration.

200. A method of ultrafiltration of a highly concentrated protein solution where the level of HMWP is suppressed to 1% or below 1% which comprises:

(a) adding sucrose to the highly concentrated protein solution when the protein concentration is between 40 g/L and 60 g/L (b) concentrate the highly concentrated protein solution by ultrafiltration.

201. A method of concentrating a highly concentrated antibody solution which comprises:

(a) adding sucrose to the highly concentrated antibody solution when the antibody concentration is between 40 g/L and 60 g/L;

(b) concentrate the highly concentrated antibody solution by ultrafiltration.

202. A method of decreasing the difference between a calculated and measured antibody concentration in a highly concentrated antibody ultrafiltration retentate which comprises:

(a) adding sucrose to the highly concentrated antibody solution when the antibody concentration is between 40 g/L and 60 g/L;

(b) concentrate the highly concentrated antibody solution by ultrafiltration.

203: A method of decreasing the difference between a calculated and measured antibody concentration in a highly concentrated antibody ultrafiltration retentate which comprises:

(a) adding sucrose to a highly concentrated antibody solution when the antibody concentration is between 40 g/L and 60 g/L (b) concentrate the highly concentrated antibody solution by ultrafiltration.

204: A method of decreasing the difference between a calculated and measured antibody concentration to less than 30% in a highly concentrated antibody ultrafiltration retentate which comprises:

(a) adding sucrose to a highly concentrated antibody solution when the antibody concentration is between 40 g/L and 60 g/L (b) concentrate the highly concentrated antibody solution by ultrafiltration.

205. A method of increasing the recovery of antibody by ultrafiltration of a highly concentrated antibody solution which comprises:

(a) adding sucrose to the highly concentrated antibody solution when the antibody concentration is between 40 g/L and 60 g/L (b) concentrate the highly concentrated antibody solution by ultrafiltration.

206. A method of increasing the recovery of antibody by ultrafiltration of a highly concentrated antibody solution to above 50% of the total amount of said antibody in the highly concentrated solution to be ultrafiltrated which comprises:

(a) adding sucrose to the highly concentrated antibody solution when the antibody concentration is between 40 g/L and 60 g/L (b) concentrate the highly concentrated antibody solution by ultrafiltration.

207. A method of stabilizing a highly concentrated antibody solution during ultrafiltration which comprises:

(a) adding sucrose to the highly concentrated antibody solution when the antibody concentration is between 40 g/L and 60 g/L (b) concentrate the highly concentrated antibody solution by ultrafiltration.

208. A method of suppressing the formation of HMWP during ultrafiltration of a highly concentrated antibody solution which comprises:

(a) adding sucrose to the highly concentrated antibody solution when the antibody concentration is between 40 g/L and 60 g/L (b) concentrate the highly concentrated antibody solution by ultrafiltration.

209. A method of ultrafiltration where the level of HMWP is suppressed to 1% or below 1% which comprises:

(a) adding sucrose to the highly concentrated antibody solution when the antibody concentration is between 40 g/L and 60 g/L (b) concentrate the highly concentrated antibody solution by ultrafiltration.

210. A method according to any of embodiments 192-209, wherein the protein or antibody concentration is between 45 g/L and 55 g/L when sucrose is added to the solution.

211. A method according to any of embodiments 192-210, wherein the sucrose is added in the concentration of between 100 mM and 300 mM.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of concentrating a protein solution, comprising the step of ultrafiltering a protein solution to generate an ultrafiltration retentate, wherein the protein solution comprises (a) sucrose in a concentration of between 50 mM and 300 mM and (b) a protein in a concentration of between 40 and 150 g/L before the step of ultrafiltering, wherein the difference between the calculated protein concentration and the measured protein concentration in the ultrafiltration retentate is decreased, wherein the protein is an antibody.

2. The method according to claim 1, wherein the difference between the calculated protein concentration and the measured protein concentration in the ultrafiltration retentate is less than 30%.

3. The method according to claim 1, wherein the addition of sucrose stabilizes the solution to be ultrafiltrated.

4. The method according to claim 1, wherein the level of HMWP aggregates is 1% or below 1% in the ultrafiltration retentate.

5. The method according to claim 1, wherein the recovery of the protein during ultrafiltration is increased as compared with the recovery of the protein during the ultrafiltration where sucrose is not added to the protein solution when the protein concentration of the solution is between 40 and 150 g/L.

6. The method according to claim 1, wherein the recovery of the protein during ultrafiltration is 94% or above, of the total amount of protein in the protein solution to be ultrafiltrated.

7. The method according to claim 1, wherein the sucrose is at a concentration of between 100 mM and 250 mM.

8. The method according to claim 1, wherein the protein is an IgG4 antibody.

9. The method according to claim 1, wherein the antibody is a monoclonal antibody.

10. The method according to claim 1, wherein the antibody is an anti-IL-20 monoclonal antibody.

11. The method according to claim 1, wherein the protein is at a concentration between 40 g/l and 60 g/l in the protein solution.

12. The method according to claim 1, wherein the sucrose is at a concentration between 100 mM and 200 mM.

13. A method of concentrating a protein solution, comprising the step of ultrafiltering a protein solution to generate an ultrafiltration retentate having a final protein concentration of between 100 g/L and 300 g/L, wherein the protein solution comprises (a) sucrose in a concentration of between 50 mM and 300 mM and (b) a protein in a concentration of between 40 and 150 g/L before the step of ultrafiltering, wherein the difference between the calculated protein concentration and the measured protein concentration in the ultrafiltration retentate is decreased, wherein the protein is an antibody.

14. The method according to claim 1, wherein the protein is at a concentration between 60 g/L and 150 g/L in the protein solution.

* * * * *